US009707064B1

(12) United States Patent
Al-Rashed et al.

(10) Patent No.: US 9,707,064 B1
(45) Date of Patent: Jul. 18, 2017

(54) DEVICE FOR VERIFYING PARALLELISM OF ABUTMENT TEETH FOR DENTAL APPLIANCE INSERTION

(71) Applicant: KING SAUD UNIVERSITY, Riyadh (SA)

(72) Inventors: Safa Mohammed Salman Al-Rashed, Riyadh (SA); Hanan Nejer Sahil Alotaibi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/393,078

(22) Filed: Dec. 28, 2016

(51) Int. Cl.
  *A61C 19/00* (2006.01)
  *A61C 8/00* (2006.01)
  *A61C 19/055* (2006.01)

(52) U.S. Cl.
  CPC .......... *A61C 19/055* (2013.01); *A61C 8/0089* (2013.01)

(58) Field of Classification Search
  CPC ..... A61C 19/055; A61C 19/04; A61C 8/0089; A61C 8/009
  USPC ............. 433/72, 74, 75; 33/513, 514, 542.1, 33/544.5; 606/218
  See application file for complete search history.

(56) References Cited

U.S. PATENT DOCUMENTS

| | | | | |
|---|---|---|---|---|
| 1,726,193 A | * | 8/1929 | Ross ..................... | A61C 13/12 433/72 |
| 2,540,555 A | * | 2/1951 | Slaughter, Jr. ......... | A61C 19/04 33/27.033 |
| 2,910,773 A | * | 11/1959 | Walton ................. | A61C 19/055 433/72 |
| 3,417,471 A | * | 12/1968 | Mitchell ............... | A61C 13/00 433/72 |
| 3,486,230 A | * | 12/1969 | Simmons ............. | A61C 13/225 433/172 |
| 4,478,580 A | * | 10/1984 | Barrut ................... | A61C 3/06 433/223 |
| 4,568,282 A | * | 2/1986 | Bogdanoff ............ | A61C 19/055 433/72 |

(Continued)

FOREIGN PATENT DOCUMENTS

| CH | 653 882 A5 | | 1/1986 | |
|---|---|---|---|---|
| CH | 653882 A5 | * | 1/1986 | ........... A61C 19/055 |

*Primary Examiner* — Yogesh Patel
*Assistant Examiner* — Meredith Shin
(74) *Attorney, Agent, or Firm* — Richard C. Liman (57) ABSTRACT

The device for verifying parallelism of abutment teeth for dental appliance insertion provides a visual indicator for a dental practitioner for determining parallelism in a pair of abutment teeth. The device for verifying parallelism of abutment teeth for dental appliance insertion includes a housing having a top end, a bottom end, and longitudinally-extending slot formed therethrough. First and second rods are received within the longitudinally-extending slot and are longitudinally slidable therein, with each of the first and second rods extending laterally (i.e., perpendicular to the longitudinal direction) through the longitudinally-extending slot. First and second plates are respectively suspended from central portions of the first and second rods and are longitudinally slidable through an opening formed through the bottom end of the housing. First and second ratcheting mechanisms respectively limit rotational movement and rotational direction of the first and second plates with respect to the housing.

19 Claims, 5 Drawing Sheets

(56) References Cited

U.S. PATENT DOCUMENTS

| | | | | |
|---|---|---|---|---|
| 4,722,686 | A | * | 2/1988 | Salib .................. A61C 19/04 433/49 |
| 5,215,460 | A | * | 6/1993 | Perry .................. A61C 19/055 433/173 |
| 5,551,873 | A | * | 9/1996 | Aiba .................. A61C 19/05 33/514 |
| 2015/0351865 | A1 | * | 12/2015 | Honig ................ A61C 8/0053 433/76 |

* cited by examiner

DEVICE FOR VERIFYING PARALLELISM OF ABUTMENT TEETH FOR DENTAL APPLIANCE INSERTION

BACKGROUND OF THE INVENTION

1. Field of the Invention

The present invention relates to the preparation and insertion of dental appliances, such as removable partial dentures and the like, and particularly to a device for verifying parallelism of abutment teeth for insertion of the dental appliance.

2. Description of the Related Art

For the accurate placement of a dental appliance, such as a fixed partial denture, for example, the parallelism of the axial walls of abutment teeth is a fundamental concern. The path of insertion of a dental appliance is expressed by the angle between the horizontal plane through the teeth and the plane tangent to the axial wall of the abutment teeth. When the abutment teeth do not have a particular inclination, the path of insertion of the dental appliance is approximately 90°. When an abutment tooth is inclined mesially, removal of an inordinate amount of tooth substance can threaten the integrity of the dental pulp. The path of insertion of the dental appliance in this case will be less than 90° and depends on the inclination of the abutment tooth. When the inclination angle of the abutment tooth is less, so is the angle of the path of insertion, thus jeopardizing the parallelism with the axial wall of the other abutment tooth.

In treatment planning, preemptive measures are instituted to determine the path of insertion to ensure parallel axial walls of abutment teeth. Commonly, for inspection by the indirect method, intraoral impressions are made and a cast is poured. The cast is examined on a laboratory surveyor and the parallelism of the abutment teeth is verified. This technique, however, suffers from the following disadvantages: it requires additional visits before the final impression is made; there is no certainty that this second appointment will ensure parallelism because the exact location and amount of tooth structure for removal requires an additional impression; and conservatism is difficult.

Conversely, direct methods use devices referred to as intraoral and extraoral parallelographs. The intraoral parallelographs have the disadvantage of an additional visit for device preparation and the extraoral parallelographs have limited stability. It would be desirable to be able to determine the parallelism directly, easily and efficiently. Thus, a device for verifying parallelism of abutment teeth for dental appliance insertion solving the aforementioned problems is desired.

SUMMARY OF THE INVENTION

The device for verifying parallelism of abutment teeth for dental appliance insertion provides a visual indicator for a dental practitioner for determining parallelism in a pair of abutment teeth. The device for verifying parallelism of abutment teeth for dental appliance insertion includes a housing having a top end, a bottom end, and longitudinally-extending slot formed therethrough. First and second rods are received within the longitudinally-extending slot and are longitudinally slidable therein, with each of the first and second rods extending laterally (i.e., perpendicular to the longitudinal direction) through the longitudinally-extending slot.

First and second plates are respectively suspended from central portions of the first and second rods and are longitudinally slidable through an opening formed through the bottom end of the housing. First and second ratcheting mechanisms respectively limit rotational direction of the first and second plates with respect to the housing. In use, the housing is positioned in a patient's mouth adjacent a pair of abutment teeth such that the first and second plates may be selectively slid to contact respective ones of the pair of abutment teeth. The first and second ratcheting mechanisms provide lockable rotation of the first and second plates with respect to the housing. This locking angular rotation of the plates allows the dental practitioner to visually inspect respective contact angles between the first and second plates and the pair of abutment teeth.

Although the above has been described with respect to the device being placed in the mouth of the patient, it should be understood that the device may also be used extraorally on a stone model of the patient's teeth. Once the proper parallelism between the guiding planes of the pair of abutment teeth are established on the stone model, the device with the obtained parallelism or relation may then be transferred to the patient's mouth until the first and second plates of the device fit passively in place. This provides an easy and efficient procedure for transferring the obtained path of insertion on the dental stone model of the patient in the lab to the patient's mouth with the highest degree of accuracy possible. By ensuring this accuracy, the chances of damaging the teeth or the surrounding oral structures will be significantly reduced.

These and other features of the present invention will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
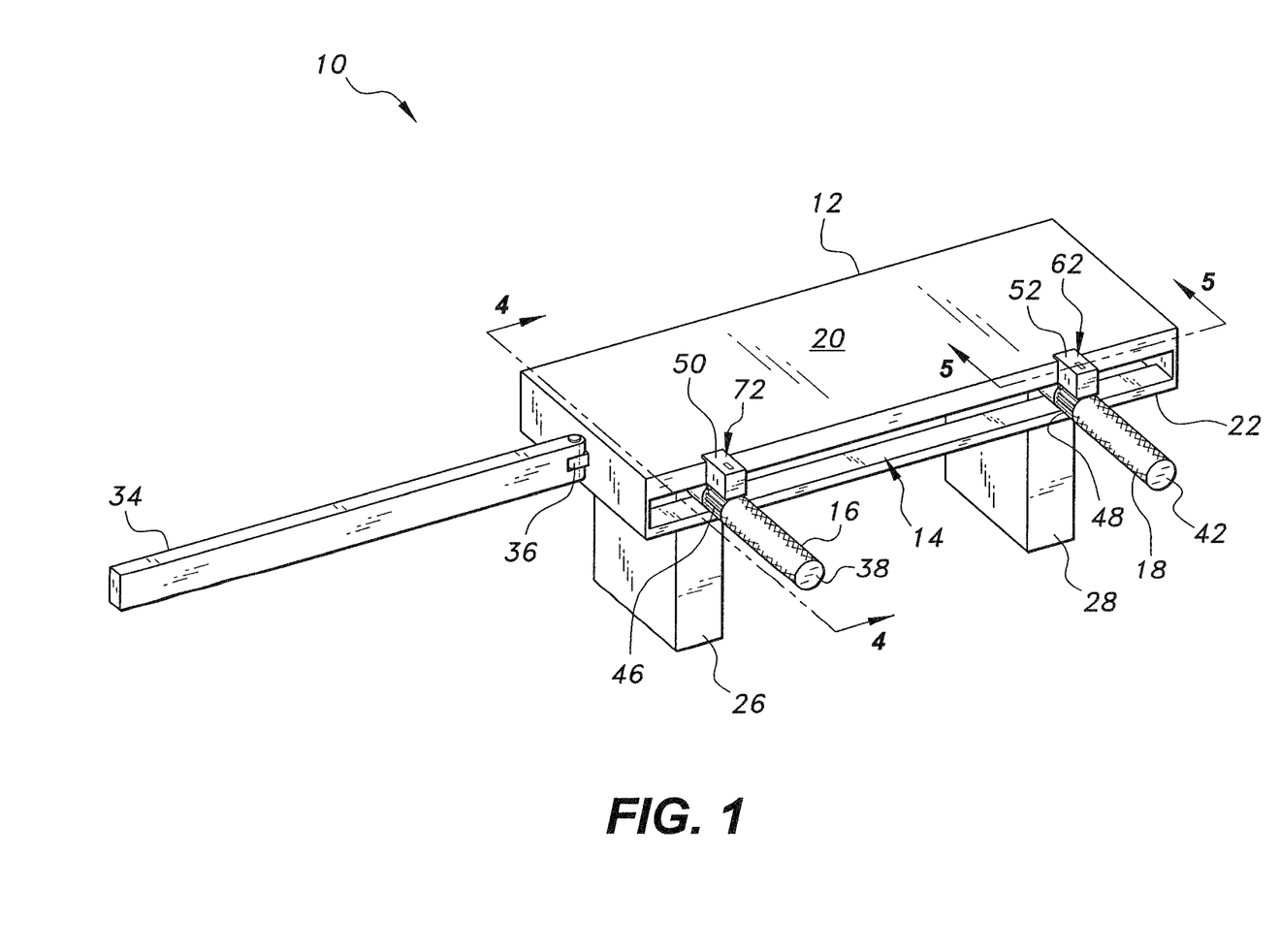
FIG. 1 is a perspective view of a device for verifying parallelism of abutment teeth for dental appliance insertion according to the present invention.
Figure 3:
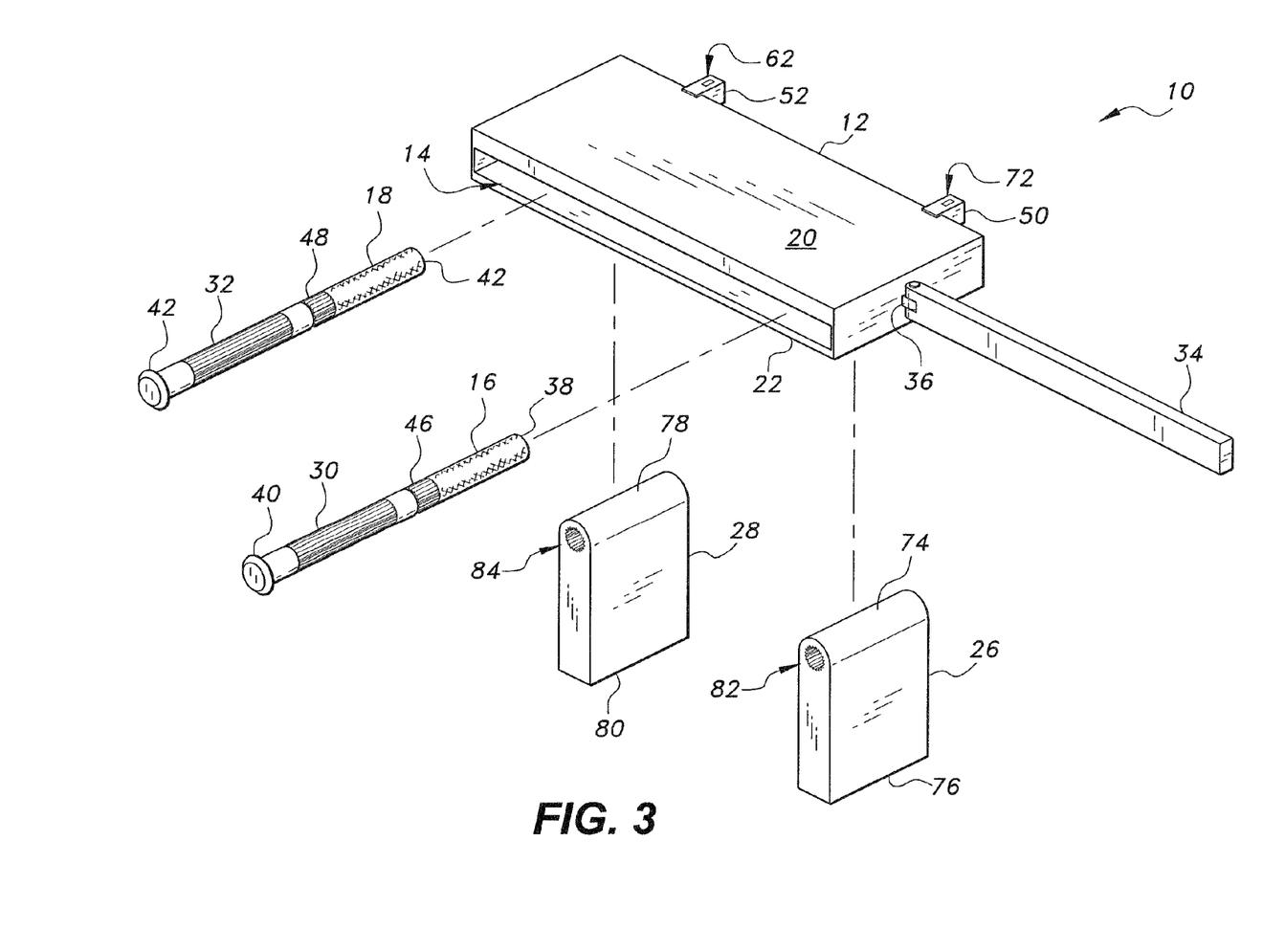
FIG. 3 is an exploded, perspective view of the device for verifying parallelism of abutment teeth for dental appliance insertion according to the present invention.

The device for verifying parallelism of abutment teeth for dental appliance insertion 10 provides a visual indicator for a dental practitioner for determining parallelism in a pair of abutment teeth. As best shown in FIGS. 1 and 3, the device for verifying parallelism of abutment teeth for dental appliance insertion 10 includes a housing 12 having a top end 20, a bottom end 22, and longitudinally-extending slot 14 formed through the housing, between top end 20 and bottom end 22. In the orientation shown in FIGS. 1 and 3, the longitudinal direction is the horizontal, left-to-right direction. As shown, a handle 34 is preferably pivotally secured to housing 12 by a hinge 36 or the like, allowing a dental practitioner to easily insert, position and remove device 10 from the patient's mouth.

First and second rods 16, 18, respectively, are received within the longitudinally-extending slot 14 and are longitudinally slidable therein, with each of the first and second rods 16, 18 extending laterally (i.e., perpendicular to the longitudinal direction) through the longitudinally-extending slot 14. As best seen in FIG. 3, first rod 16 has laterally opposed proximal and distal ends, 38, 40, respectively, with the proximal end 38 being adapted for gripping by the dental practitioner, preferably via texturing, as illustrated, providing a frictional gripping surface for the dental practitioner's fingers. The distal end of the first rod 16 defines an end cap, as shown, for preventing lateral movement of the first rod 16 through the longitudinally-extending slot 14 in order to prevent the first rod 16 from becoming dislodged from housing 12. Second rod 18 is similarly constructed, with laterally opposed proximal and distal ends, 42, 44, respectively, with the proximal end 42 being adapted for gripping by the dental practitioner in a manner identical to that of first rod 16. The distal end 44 of the second rod 18 also defines an identical end cap, as shown, for preventing lateral movement of the second rod 18 through the longitudinally-extending slot 14.

Figure 4:
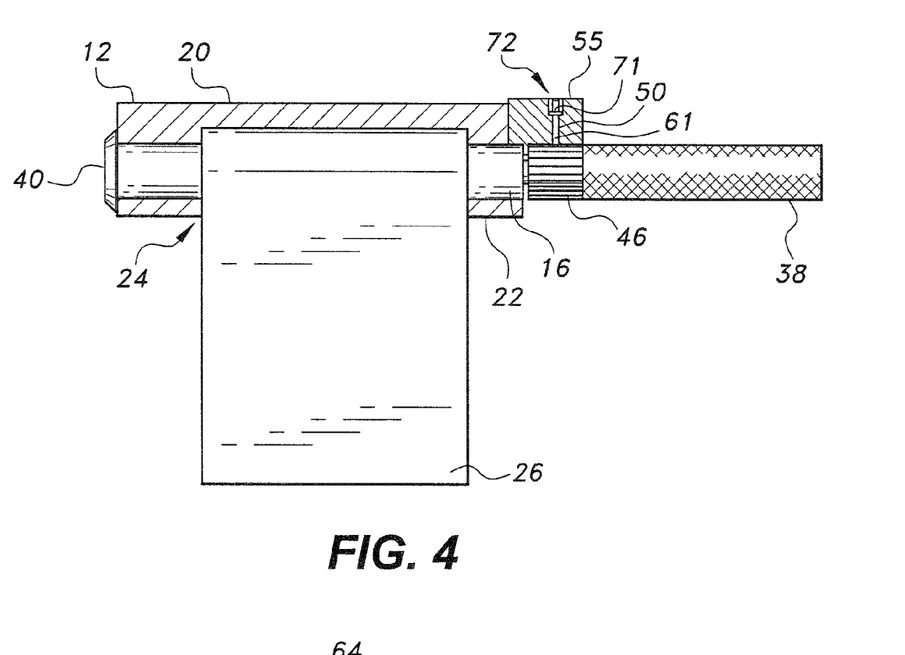
FIG. 4 is a cross-sectional view of the device for verifying parallelism of abutment teeth for dental appliance insertion, taken along section lines 4-4 of FIG. 1.

First and second plates 26, 28, are respectively suspended from central portions 30, 32 of the first and second rods 16, 18 and are longitudinally slidable through an opening 24 formed through the bottom end 22 of housing 12 (as shown in FIG. 4). First and second ratcheting mechanisms 50, 52 respectively limit rotational movement and direction of the first and second plates 26, 28 with respect to the housing 12.

Figure 5:
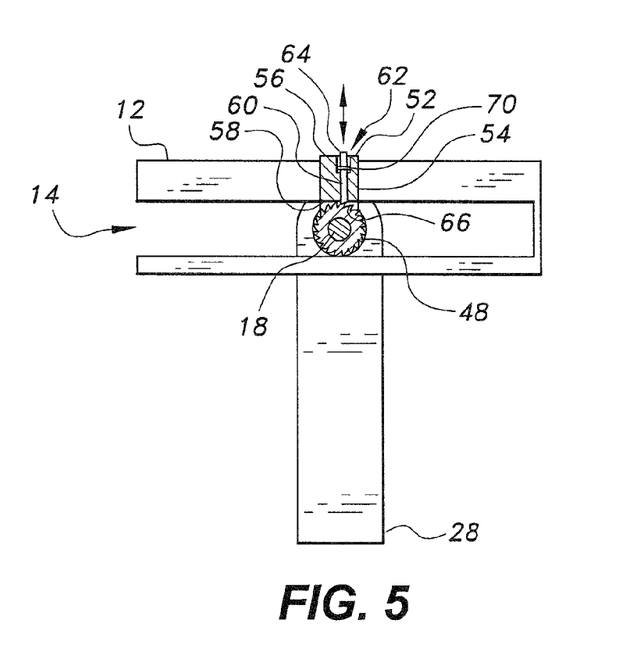
FIG. 5 is a partial cross-sectional view of the device for verifying parallelism of abutment teeth for dental appliance insertion, taken along section lines 5-5 of FIG. 1.

As best seen in FIG. 3, each of the first and second rods 16, 18 has a gear portion 46, 48, respectively, formed adjacent the respective proximal end 38, 42. As best shown in FIG. 5, ratcheting mechanism 52 includes a ratchet housing 54 having a top end 56 and an open bottom end 58. As shown, the top end 56 has an aperture 62 formed therethrough. A pawl 60, having a top end 64 and a bottom end 66, is received within ratchet housing 54 such that the top end 64 extends through the aperture 62. The bottom end 66 engages the gear portion 48 of second rod 18, with pawl 60 being vertically movable with respect to the ratchet housing 54, as in a conventional ratchet. It should be understood that pawl 60 may be spring-biased, as in a conventional ratchet, and that ratcheting mechanism 52 may be replaced by any suitable type of ratcheting mechanism, as is well-known in the art. Further, although FIG. 5 illustrates only ratcheting mechanism 52, it should be understood that ratcheting mechanism 50 operates in an identical manner for engaging gear portion 46 of first rod 16 (as illustrated in FIG. 4). In FIG. 4, pawl 61 of ratcheting mechanism 50 engages gear portion 46 and is vertically moveable within ratchet housing 55. An upper end of pawl 61 projects through an aperture 72, formed in the top end of ratchet housing 55, operating in an identical manner to that described above with respect to ratcheting mechanism 52. Further, each of first and second ratcheting mechanisms 50, 52 may also include a stop 71, 70, respectively, which is secured to the respective pawl 61, 60, adjacent the top end thereof. The stop 71, 70, which may be in the form of a gasket or the like, prevents the pawl 61, 60 from leaving the respective ratchet housing 55, 54.

Additionally, as shown in FIG. 3, the central portions 30, 32 of first and second rods 16, 18, respectively, may be grooved or striated along the lateral direction. First plate 26 has opposed top and bottom ends 74, 76, respectively, with a laterally-extending passage 82 formed through the top end 74 such that the central portion 30 of first rod 16 is received therein. As shown, the passage 82 preferably has a ratchet gear-type contour, thus allowing the central portion 30 to releasably lock in place therein. When first plate 26 is rotated during use, as will be described below, both first ratcheting mechanism 50 and the releasable locking of central portion 30 within passage 82 allow device 10 to be removed from the patient's mouth with the angle of first plate 26 remaining unchanged so that the dental practitioner can visually inspect the recorded angle. In an identical manner, second plate 28 has opposed top and bottom ends 78, 80, respectively, with a laterally-extending passage 84 formed through the top end 78 so that central portion 32 of second rod 18 is received therein. Similarly, the passage 84 has a ratchet gear-type contour, allowing the central portion 32 to releasably lock in place therein. When first plate 28 is rotated during use both the second ratcheting mechanism 52 and the releasable locking of central portion 32 within passage 84 allow device 10 to be removed from the patient's mouth with the angle of second plate 28 remaining unchanged.

Figure 2A:
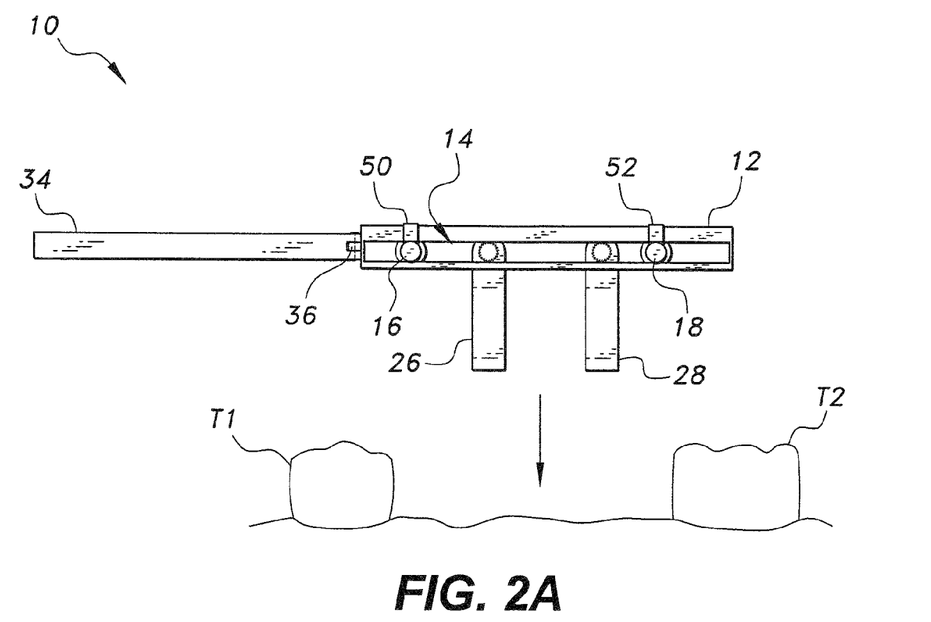
FIGS. 2A, 2B, 2C and 2D illustrate usage of the device for verifying parallelism of abutment teeth for dental appliance insertion within a patient's mouth.
Figure 2B:
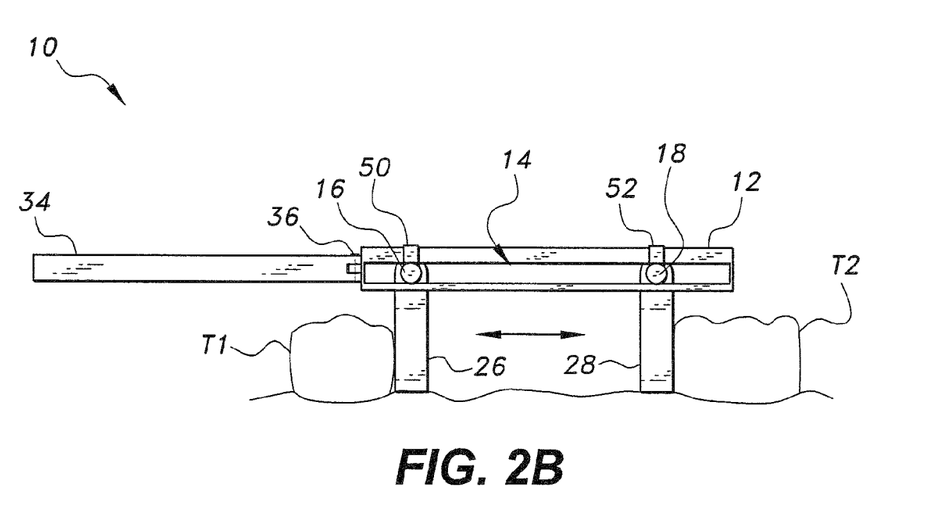
Figure 2C:
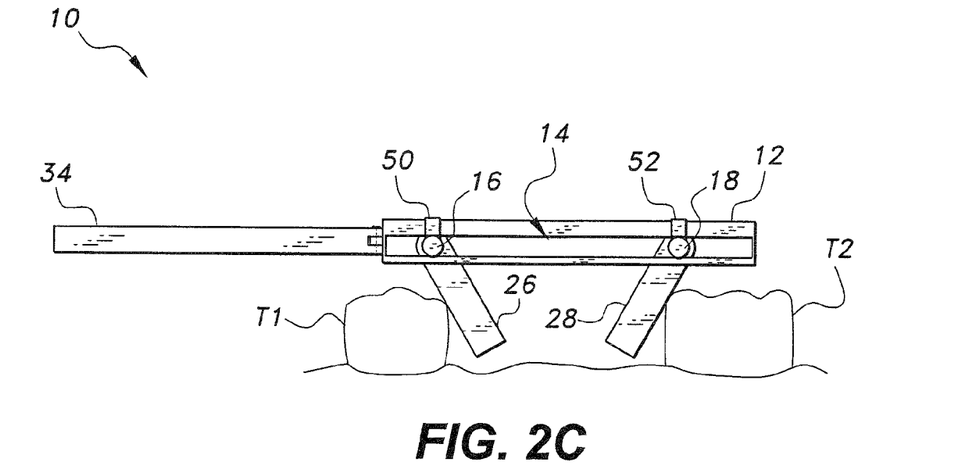

In use, as shown in FIG. 2A, the housing 12 of device 10 is positioned in a patient's mouth adjacent a pair of abutment teeth T1, T2. As noted above, the dental practitioner may use handle 34 to properly insert device 10, and position device 10 above the gap between abutment teeth T1, T2, within the patient's mouth. As shown in FIGS. 2A and 2B, the first and second plates 26, 28 initially begin with a separation therebetween which is less than the width of the gap between abutment teeth T1, T2. As shown in FIG. 2A, the first and second plates 26, 28 are then selectively slid to contact respective ones of the pair of abutment teeth T1, T2. The dental practitioner manually adjusts the horizontal movement of first and second plates 26, 28 by sliding first and second rods 16, 18 within slot 14 formed through housing 12. As shown in FIG. 2C, the plates 26, 28 are slid just far apart enough from one another that the contact angles with the tooth surfaces are recorded.

It is important to note that FIG. 2C shows a pre-procedure case in which teeth T1, T2 have not been worked on, thus presenting a case in which parallelism therebetween does not exist. Following any necessary work on teeth T1, T2, e.g., modifications on the surface of the teeth that contacts the plates to make the plates as parallel as possible, the device 10 is used again in an identical manner to determine the parallelism of teeth T1, T2 with both first and second plates 26, 28 remaining parallel with respect to one another and projecting downwardly in the vertical direction (i.e., perpendicular to housing 12).

Figure 2D:
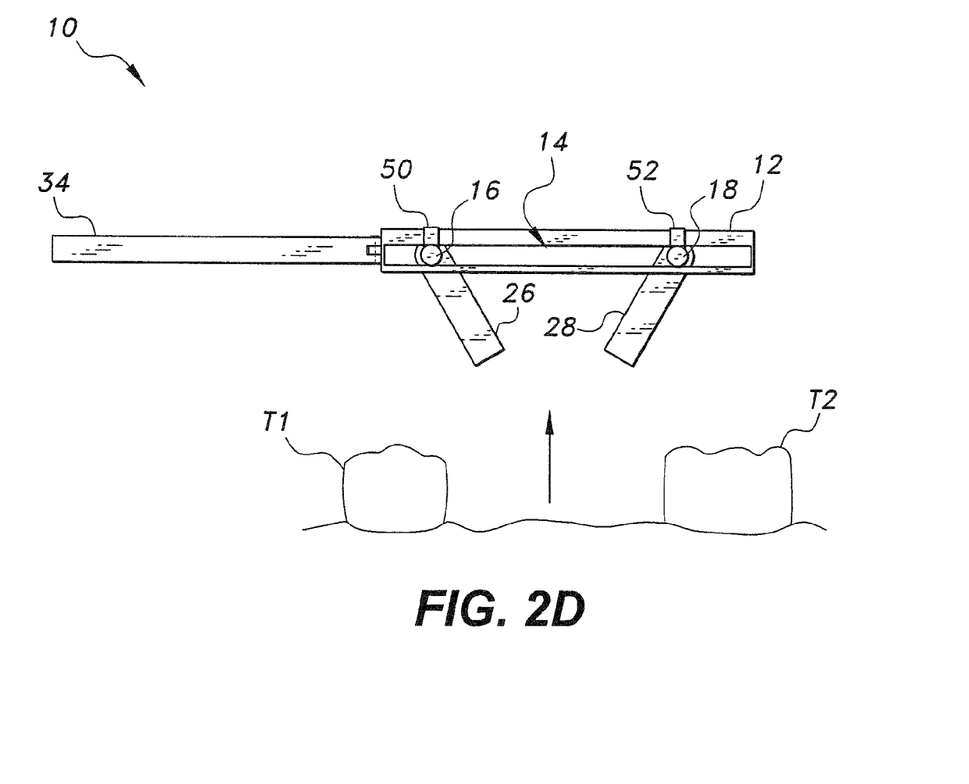

As shown in FIG. 2D, the first and second ratcheting mechanisms 50, 52 provide lockable rotation of the first and second plates 26, 28 with respect to the housing 12 (as described in detail above). This locking angular rotation of the plates 26, 28 allows the dental practitioner to visually inspect respective contact angles between the first and second plates 26, 28 and the pair of abutment teeth T1, T2 once the device 10 is removed from the mouth. Although the above has been described with respect to device 10 being placed in the mouth of the patient, it should be understood that device 10 may also be used extraorally on a stone model of the patient's teeth. Once the proper parallelism between the guiding planes of teeth T1, T2 are established on the stone model, the device 10 with the obtained parallelism or relation may then be transferred to the patient's mouth until plates 26, 28 of device 10 fit passively in place.

It should be understood that the device for verifying parallelism of abutment teeth for dental appliance insertion 10 may be manufactured from any suitable type of autoclavable material, such as metal or plastic. Further, device 10 may be used for both maxillary and mandibular posterior and anterior teeth.

It is to be understood that the present invention is not limited to the embodiments described above, but encompasses any and all embodiments within the scope of the following claims.

We claim:

1. A device for verifying parallelism of abutment teeth for dental appliance insertion, comprising:
   a housing having a top end, a bottom end, and longitudinally-extending slot formed therethrough;
   first and second rods received within the longitudinally-extending slot and being longitudinally slidable therein, wherein each of said first and second rods extends laterally through the longitudinally-extending slot;
   first and second plates respectively suspended from central portions of said first and second rods and being longitudinally slidable through an opening formed through the bottom end of said housing, wherein each of said first and second plates has a top end and a bottom end, a laterally-extending passage being formed through the top end such that the respective central portions of said first and second rods are respectively received in the laterally-extending passages of said first and second plates; and
   first and second ratcheting mechanisms for respectively limiting rotational movement and rotational direction of said first and second plates with respect to the housing,
   whereby said housing is adapted for positioning in a patient's mouth adjacent a pair of abutment teeth such that said first and second plates may be selectively slid to contact respective ones of the pair of abutment teeth, said first and second ratcheting mechanisms providing lockable rotation of said first and second plates with respect to said housing, such that a dental practitioner may visually inspect respective contact angles between the first and second plates and the pair of abutment teeth.

2. The device for verifying parallelism of abutment teeth for dental appliance insertion as recited in claim 1, further comprising a handle secured to said housing.

3. The device for verifying parallelism of abutment teeth for dental appliance insertion as recited in claim 2, wherein the handle is pivotally secured to said housing.

4. The device for verifying parallelism of abutment teeth for dental appliance insertion as recited in claim 1, wherein each of said first and second rods has laterally opposed proximal and distal ends, each said proximal end being adapted for gripping by the dental practitioner.

5. The device for verifying parallelism of abutment teeth for dental appliance insertion as recited in claim 4, wherein each said distal end of said first and second rods defines an end cap for preventing lateral movement of said first and second rods through the longitudinally-extending slot.

6. The device for verifying parallelism of abutment teeth for dental appliance insertion as recited in claim 5, wherein each of said first and second rods has a gear portion formed adjacent the respective proximal end thereof.

7. The device for verifying parallelism of abutment teeth for dental appliance insertion as recited in claim 6, wherein each of said first and second ratcheting mechanisms comprise:
   a ratchet housing having a top end and an open bottom end, the top end having an aperture formed therethrough;
   a pawl having a top end and a bottom end, the top end thereof extending through the aperture, the bottom end thereof engaging the gear portion of a respective one of said first and second rods, said pawl being vertically movable with respect to the ratchet housing.

8. The device for verifying parallelism of abutment teeth for dental appliance insertion as recited in claim 7, wherein each of said first and second ratcheting mechanisms further comprise a stop secured to the pawl, adjacent the top end thereof, for preventing the pawl from leaving the ratchet housing.

9. A device for verifying parallelism of abutment teeth for dental appliance insertion, comprising:
   a housing having a top end, a bottom end, and longitudinally-extending slot formed therethrough;
   first and second rods received within the longitudinally-extending slot and being longitudinally slidable therein, wherein each of said first and second rods extends laterally through the longitudinally-extending slot;
   first and second plates each having a top end and a bottom end, a laterally-extending passage being formed through each said top end such that a respective central portion of a corresponding one of said first and second rods is received therethrough, such that said first and second plates are respectively suspended from the central portions of said first and second rods and are longitudinally slidable through an opening formed through the bottom end of said housing, wherein each of said first and second plates has a top end and a bottom end, a laterally-extending passage being formed through the top end such that the respective central portions of said first and second rods are respectively received in the laterally-extending passages of said first and second plates; and
   first and second ratcheting mechanisms for respectively limiting rotational movement and rotational direction of said first and second plates with respect to the housing,
   whereby said housing is adapted for positioning in a patient's mouth adjacent a pair of abutment teeth such that said first and second plates may be selectively slid to contact respective ones of the pair of abutment teeth, said first and second ratcheting mechanisms providing lockable rotation of said first and second plates with respect to said housing, such that a dental practitioner may visually inspect respective contact angles between the first and second plates and the pair of abutment teeth.

10. The device for verifying parallelism of abutment teeth for dental appliance insertion as recited in claim 9, further comprising a handle secured to said housing.

11. The device for verifying parallelism of abutment teeth for dental appliance insertion as recited in claim 10, wherein the handle is pivotally secured to said housing.

12. The device for verifying parallelism of abutment teeth for dental appliance insertion as recited in claim 9, wherein each of said first and second rods has laterally opposed proximal and distal ends, each said proximal end being adapted for gripping by the dental practitioner.

13. The device for verifying parallelism of abutment teeth for dental appliance insertion as recited in claim 12, wherein each said distal end of said first and second rods defines an end cap for preventing lateral movement of said first and second rods through the longitudinally-extending slot.

14. The device for verifying parallelism of abutment teeth for dental appliance insertion as recited in claim 13, wherein each of said first and second rods has a gear portion formed adjacent the respective proximal end thereof.

15. The device for verifying parallelism of abutment teeth for dental appliance insertion as recited in claim 14, wherein each of said first and second ratcheting mechanisms comprise:
- a ratchet housing having a top end and an open bottom end, the top end having an aperture formed therethrough;
- a pawl having a top end and a bottom end, the top end thereof extending through the aperture, the bottom end thereof engaging the gear portion of a respective one of said first and second rods, said pawl being vertically movable with respect to the ratchet housing.

16. The device for verifying parallelism of abutment teeth for dental appliance insertion as recited in claim 15, wherein each of said first and second ratcheting mechanisms further comprise a stop secured to the pawl, adjacent the top end thereof, for preventing the pawl from leaving the ratchet housing.

17. A device for verifying parallelism of abutment teeth for dental appliance insertion, comprising:
- a housing having a top end, a bottom end, and longitudinally-extending slot formed therethrough;
- first and second rods received within the longitudinally-extending slot and being longitudinally slidable therein, wherein each of said first and second rods extends laterally through the longitudinally-extending slot, each of said first and second rods having laterally opposed proximal and distal ends, each said proximal end being adapted for gripping by the dental practitioner, each said distal end defining an end cap for preventing lateral movement of said first and second rods through the longitudinally-extending slot, and a gear portion being formed on each of said first and second rods adjacent the respective proximal end thereof;
- first and second plates respectively suspended from central portions of said first and second rods and being longitudinally slidable through an opening formed through the bottom end of said housing; and
- first and second ratcheting mechanisms for respectively engaging the gear portions of said first and second rods for limiting rotational movement and rotational direction of said first and second plates with respect to the housing,
- whereby said housing is adapted for positioning in a patient's mouth adjacent a pair of abutment teeth such that said first and second plates may be selectively slid to contact respective ones of the pair of abutment teeth, said first and second ratcheting mechanisms providing lockable rotation of said first and second plates with respect to said housing, such that a dental practitioner may visually inspect respective contact angles between the first and second plates and the pair of abutment teeth.

18. The device for verifying parallelism of abutment teeth for dental appliance insertion as recited in claim 17, wherein each of said first and second ratcheting mechanisms comprise:
- a ratchet housing having a top end and an open bottom end, the top end having an aperture formed therethrough;
- a pawl having a top end and a bottom end, the top end thereof extending through the aperture, the bottom end thereof engaging the gear portion of a respective one of said first and second rods, said pawl being vertically movable with respect to the ratchet housing.

19. The device for verifying parallelism of abutment teeth for dental appliance insertion as recited in claim 18, wherein each of said first and second ratcheting mechanisms further comprise a stop secured to the pawl, adjacent the top end thereof, for preventing the pawl from leaving the ratchet housing.

* * * * *